(12) United States Patent
Compadre et al.

(10) Patent No.: US 11,116,746 B2
(45) Date of Patent: Sep. 14, 2021

(54) USE OF RICE BRAN OIL DISTILLATE EXTRACT FOR PREVENTION AND MITIGATION OF THE EFFECTS OF RADIATION

(71) Applicant: Tocol Pharmaceuticals, LLC, Little Rock, AR (US)

(72) Inventors: Cesar M. Compadre, Little Rock, AR (US); Philip Breen, Little Rock, AR (US); Nukhet Aykin-Burns, Little Rock, AR (US); Martin Hauer-Jensen, Little Rock, AR (US)

(73) Assignee: Tocol Pharmaceuticals, LLC, Little Rock, AR (US)

( * ) Notice: Subject to any disclaimer, the term of this patent is extended or adjusted under 35 U.S.C. 154(b) by 211 days.

(21) Appl. No.: 16/246,012

(22) Filed: Jan. 11, 2019

(65) Prior Publication Data

US 2019/0142791 A1 May 16, 2019

Related U.S. Application Data

(63) Continuation of application No. 15/147,230, filed on May 5, 2016, now abandoned.

(60) Provisional application No. 62/157,383, filed on May 5, 2015.

(51) Int. Cl.
| | |
|---|---|
| *A61K 31/353* | (2006.01) |
| *A61K 45/06* | (2006.01) |
| *A61K 31/01* | (2006.01) |
| *A61K 36/899* | (2006.01) |
| *A61K 47/20* | (2006.01) |

(52) U.S. Cl.
CPC ............ *A61K 31/353* (2013.01); *A61K 31/01* (2013.01); *A61K 36/899* (2013.01); *A61K 45/06* (2013.01); *A61K 47/20* (2013.01)

(58) Field of Classification Search
CPC .. A61K 2300/00; A61K 31/01; A61K 31/353; A61K 36/899; A61K 45/06; A61K 47/20
See application file for complete search history.

(56) References Cited

U.S. PATENT DOCUMENTS

| | | |
|---|---|---|
| 4,168,271 A | 9/1979 | Cardenas |
| 5,114,957 A | 5/1992 | Hendler |
| 5,336,485 A | 8/1994 | Fariss |
| 5,591,772 A | 1/1997 | Lane |
| 5,606,080 A | 2/1997 | Ogata |
| 5,821,264 A | 10/1998 | Lane |
| 5,827,878 A | 10/1998 | Makishima |
| 5,919,818 A | 7/1999 | Lane |
| 5,929,057 A | 7/1999 | Makishima |
| 5,990,322 A | 11/1999 | Lee |
| 6,133,312 A | 10/2000 | Elson |
| 6,143,770 A | 11/2000 | Lane |
| 6,204,290 B1 | 3/2001 | Lane |
| 6,239,171 B1 | 5/2001 | Lane |
| 6,350,453 B1 | 2/2002 | Tan |
| 6,395,915 B1 | 5/2002 | Bellafiore |
| 6,410,752 B1 | 6/2002 | Kim |
| 6,417,223 B1 | 7/2002 | Sanders |
| 6,683,194 B2 | 1/2004 | Zhang |
| 6,716,873 B1 | 4/2004 | Keramidas |
| 6,770,672 B1 | 8/2004 | Sanders |
| 7,105,686 B2 | 9/2006 | Giraudi |
| 7,642,064 B2 | 1/2010 | Bieniarz |
| 7,799,782 B2 | 9/2010 | Munson |
| 8,044,161 B2 | 10/2011 | Tiitinen |
| 9,309,547 B2 | 4/2016 | Zheng |
| 9,512,098 B1 * | 12/2016 | Howard ............... C07D 311/72 |
| 9,993,456 B2 | 6/2018 | Compadre |
| 2005/0037102 A1 | 2/2005 | Tan |
| 2009/0036354 A1 | 2/2009 | Gavin |
| 2009/0041870 A1 | 2/2009 | Tan |
| 2010/0003716 A1 | 1/2010 | Cervin |
| 2010/0036079 A1 | 2/2010 | Tiitinen |
| 2011/0293753 A1 | 12/2011 | Bellafiore |
| 2013/0158106 A1 | 6/2013 | Breen |
| 2015/0087033 A1 | 3/2015 | Zheng |

FOREIGN PATENT DOCUMENTS

| | | |
|---|---|---|
| DE | 202013005637 | 7/2013 |
| WO | 1993009777 | 5/1993 |
| WO | 2000016772 | 3/2000 |
| WO | 2000071531 | 7/2000 |
| WO | 2001058889 | 8/2001 |
| WO | 2003039461 | 5/2003 |
| WO | 2009126866 | 10/2009 |
| WO | 2011001258 | 1/2011 |
| WO | 2011150312 | 12/2011 |
| WO | 2011153353 | 12/2011 |
| WO | 2013176745 | 11/2013 |
| WO | 2015039029 | 3/2015 |

OTHER PUBLICATIONS

"Annatto Tocotrienols" www.cpmedical.net/pdf/TS_CP3093AnnattoTocotrienols.pdf.

Berbee, M. et al., "γ-Tocotrienol ameliorates intestinal radiation injury and reduces vascular oxidative stress after total-body irradiation by an HMG-CoA reductase-dependent mechanism," (2009) Radiation Research 171:596-605.

Buss, A.W. "Diastereoselective synthesis of alpha-tocopherol," Inaugural dissertation, Basel Nov. 11, 2008.

Cesar M. Compadre Declaration Under 37 C.F.R. §1.132, Sep. 8, 2017.

Frega, N. et al., "Identification and Estimation of Tocotrienols in the Annatoo Lipid Fraction by Gas Chromatography-Mass Spectrometry" J. Am. Oil Chem. Soc., 1998, 75(12), 1723-1727.

(Continued)

*Primary Examiner* — Umamaheswari Ramachandran
(74) *Attorney, Agent, or Firm* — Quarles & Brady LLP (57) ABSTRACT

Provided herein is a tocol rich fraction of rice bran oil deodorized distillate that is shown to be both radioprotective and able to protect against oxidative damage. This fraction may prove an inexpensive and readily available extract that can be used to prepare pharmaceutical compositions for use in protecting against radiation exposure and/or other forms of oxidative stress.

18 Claims, 6 Drawing Sheets

(56) References Cited

OTHER PUBLICATIONS

Ghosh, S.P. et al., "Chemistry of tocotrienols," (2009) Tocotrienols: Vitamin E beyond tocopherols, CRC Press, Edited by Ronald Ross Watson and Victor R. Preedy, 7:85-96.
Ghosh, S.P. et al., "Gamma-tocotrienol, a tocol antioxidant as a potent radioprotector," (2009) Int. J. Radiat. Biol. 85(7):598-606.
International Search Report and Written Opinion for International Application No. PCT/US2011/038933 dated Sep. 12, 2011 (11 pages).
International Search Report and Written Opinion for International Application No. PCT/US2013/030862 dated May 28, 2013 (20 pages).
International Search Report and Written Opinion for International Application No. PCT/US2014/055657 dated Dec. 22, 2014 (10 pages).
Jondiko, I.J.O., et al., "Terpenoids and an apocarotenoid from seeds of Bixa orellana" 1989 Phytochemistry 28(11): 3159-3162.
Kelly, Gregory S. "Squalene and its potential clinical uses." Alternative medicine review: a journal of clinical therapeutic 4.1 (1999): 29.
Ko, S. N. et al., "The Concentration of Tocols from Rice Brain Oil Deodorizer Distillate Using Solvent," (2008) Eur. J. Technol. 110:914-919.
Krager, K. et al., "Tocotrienol-Rich Fraction from Rice Bran Demonstrates Potent Radiation Protection Activity," (2015) Evidence-Based Complementary and Alternative Medicine, 1-9.
Kumar, K. S. et al., "Gamma-tocotrienol: Potential as a countermeasure against radiological threat," (2009) Tocotrienols: Vitamin E beyond tocopherols, CRC Press, Edited by Ronald Ross Watson and Victor R. Preedy, 27:379-398.
Leonard, S.W. et al., Studies in humans using deuterium-labeled a- and g-tocopherols demonstrate faster plasma g-tocopherol disappearance and greater g-metabolite production 2005 Free Radical Biology and Medicine 38(7):857-866.
Leth, T. et al., "Biological activity of Vitamin E compounds and natural materials by the resorption-gestation test, and chemical determination of the Vitamin E activity in foods and feeds," (1977) J. Nutr. 107:2236-2243.
Nowak, G. et al., GT3 protects against mitochondrial dysfunction 2012 Journal of Pharmacology and Experimental Therapeutics, 340:330-338.
Odinokov, et al. "Synthesis of a-tocopherol (vitamin E), vitamin K1-chromanol, and their analogs in the presence of aluminosilicate catalysts Tseokar-10 and Pentasil" (ARKIVOC, 2003 (xiii) 101-118).
Office Action for U.S. Appl. No. 13/701,630 dated Aug. 12, 2015 (27 pages).
Office Action for U.S. Appl. No. 13/701,630 dated Dec. 31, 2014 (23 pages).
Office Action for U.S. Appl. No. 13/701,630 dated Jan. 10, 2017 (13 pages).
Office Action for U.S. Appl. No. 13/701,630 dated Jun. 1, 2016 (25 pages).
Office Action for U.S. Appl. No. 13/701,630 dated Mar. 10, 2014 (19 pages).
Office Action for U.S. Appl. No. 13/701,630 dated Nov. 2, 2017 (20 pages).
Office Action for U.S. Appl. No. 14/402,792 dated Aug. 5, 2015 (11 pages).
Office Action for U.S. Appl. No. 15/021,376 dated Mar. 9, 2017 (27 pages).
Office Action for U.S. Appl. No. 15/021,376 dated Nov. 16, 2017 (12 pages).
Office Action for U.S. Appl. No. 15/147,230 dated Apr. 21, 2017 (12 pages).
Office Action for U.S. Appl. No. 15/147,230 dated Dec. 28, 2017 (15 pages).
Office Action for U.S. Appl. No. 15/147,230 dated Oct. 11, 2016 (23 pages).
Office Action for U.S. Appl. No. 15/147,230 dated Oct. 11, 2018 (21 pages).
Panagabko, C. et al., "Ligand specificity in the CRAL-TRIO protein family," (2003) Biochem 42:6467-6474.
Puah, et al., "The effect of physical refining on palm vitamin E," tocopherol, tocotrienol and tocomonoenol, American Journal of Applied Sciences (2007) 4(6):374-377.
Quereshi, A.A. et al., Dietary alpha tocopherols attenuates the impact of gamma tocotrienols on hepatic 3-hydroxy-3-methylglutaryl coenzyme A reductase activity in chickens 1996 J. Nutri.126(2):389-394.
Rammell, et al., "Separation of tocols by HPLC on an amino-cyano polar phase column," J. of Liquid Chromatography (1985) 8(4):707-717.
Singh, V.K. et al., Radioprotective Efficacy of Gamma-Tocotrienol in Nonhuman Primates 2016 Radiation Research 185:285-298.
Singh, V.K., et al. "Vitamin E: tocopherols and tocotrienols as potential radiation countermeasures" Journal of Radiation Research, 2013, pp. 973-988, vol. 54.
Uchida, Tomono, et al., "Tissue Distribution of alpha- and gamma-Tocotrienol and gamma-Tocopherol in Rats and Interference with Their Accumulation by alpha-Tocopherol" Lipids, 2012, 47:129-139.
Yap, S.P. et al., Pharmacokinetics and bioavailability of alpha, gamma and delta-tocotrienols under different food status 2001 J. Pharmacy and Pharmacology 53:67-71.

\* cited by examiner

USE OF RICE BRAN OIL DISTILLATE EXTRACT FOR PREVENTION AND MITIGATION OF THE EFFECTS OF RADIATION

CROSS-REFERENCE TO RELATED APPLICATIONS

This patent application claims the benefit of priority of U.S. patent application Ser. No. 15/147,230, filed May 5, 2016, and U.S. Provisional Patent Application No. 62/157,383, filed May 5, 2015, the contents of which is incorporated herein by reference in its entirety.

INTRODUCTION

Vitamin E is composed of eight naturally occurring tocols. Four are tocopherols, which possess a saturated hydrocarbon tail, and four are tocotrienols, which possess three trans double bonds in the hydrocarbon tail. The tocols are known to have beneficial health effects when provided as a dietary supplement. The tocotrienols have recently been shown to have beneficial health effects not seen with the tocopherols.

Commercially available tocotrienols are purified from natural oils, where they occur as complex mixtures of tocotrienols and tocopherols. It is very difficult to separate the pure tocotrienols from these mixtures and therefore these compounds are very expensive.

This invention relates to the preparation of a composition from rice bran oil deodorized distillate containing tocotrienols and other compounds and its use in a dose effective to prevent and mitigate the effects of radiation and prevent oxidative damage.

SUMMARY

Provided herein is a method of preparing a composition having tocotrienols. Further, a method of purification, enrichment, and standardization is described which results in a dose that shows effective radioprotective activity and prevents oxidative damage without toxicity. Finally, we present a composition, which shows synergism over and above the effect shown by the individual tocotrienol constituents. Also provided are the compositions and methods of using the compositions. First, the oil is extracted from rice bran oil deodorized distillate. Then, the tocotrienols are separated from the extract via chromatography.

In one aspect, pharmaceutical compositions having a total tocotrienol content between 15% and 95% are provided. Suitably at least 30%, 40%, 45%, 50%, 55%, 60%, 70%, 80%, 90% or 95% of the composition is tocotrienols.

In another aspect, methods of treating a subject with a condition are provided. The methods include administering an effective amount of at least one of the described compositions to the subject to ameliorate the condition. The subject may be in need of treatment with a radioprotectant or for treatment of radiation exposure. The subject may be in need of an antioxidant, an anti-inflammatory agent, an immunoregulatory agent, an anti-thrombotic agent, an anti-atherogenic agent, a hypocholesterolemic agent or an HMG-CoA reductase inhibitor. The subject may have a condition selected from radiation exposure, cancer, cardiovascular disease including but not limited to coronary artery disease, elevated lipoprotein levels, elevated cholesterol levels, elevated triglycerides, age-related macular degeneration, cataracts, glaucoma, chronic pain, chronic fatigue syndrome, fever, edema, diabetes mellitus, signs of aging, rheumatoid diseases, septic shock, and Alzheimer's disease.

In a still further aspect, methods of protecting cells from oxidative damage or radiation exposure are provided. The methods include contacting the cells with the pharmaceutical compositions provided herein to protect the cells from oxidative damage or radiation exposure. The cells may be contacted with the pharmaceutical composition before, during or after the oxidative damage or radiation exposure.

BRIEF DESCRIPTION OF THE DRAWINGS

FIG. 4 shows a set of graphs to demonstrate that pre-treatment with 5 μM DT3 or TRFRB preserved the cellular bioenergetics and mitochondrial respiration of H9c2 cells following $H_2O_2$ injury. Treatment with both DT3 (delta-tocotrienol) and TRFRB increased basal oxygen consumption rate (OCR) as well as maximum OCR in H9c2 rat heart cardiomyocytes (FIG. 4A). Treatment with DT3 or TRFRB prior to 50 μM $H_2O_2$ (FIG. 4B) or 100 μM $H_2O_2$ (FIG. 4C) resulted in complete protection and restored the mitochondrial respiration. Each data point represents mean±SEM of n=8-16 wells from 2 separate experiments. *$p<0.01$ as compared to Control, #$p<0.001$ as compared to $H_2O_2$ treated group.

FIG. 5 is a graph showing the response of cells to radiation damage.

DETAILED DESCRIPTION

Radiation therapy used in the definitive management and palliative care of cancer patients frequently results in acute and late radiation-induced normal tissue toxicity. More than 50% of cancer patients receive radiotherapy alone or in combination with chemotherapy or surgery in order to achieve local or regional control of their malignancies. Although ionizing radiation (IR) is very effective for killing cancer cells, patients continue to suffer from acute and chronic adverse side effects that limit the therapeutic window for radiotherapy. In addition, significant growth in nuclear power production and radionuclide usage increases the risk of radiation exposure to large populations. Radiation exposure through inadvertent release of nuclear material, such as the Fukishima reactor, is additionally problematic and few treatment options are available. Therefore there is an imminent need for safe and effective radioprotectors to improve the quality of life in patients who receive radiotherapy or are exposed to radiation.

IR exposure causes significant increases in generation of reactive oxygen and nitrogen species (ROS/RNS), such as superoxide, hydrogen peroxide ($H_2O_2$), and peroxynitrite. Alterations in redox homeostasis caused by these reactive species damage the DNA and intracellular compartments leading to perturbations in biochemical reactions and critical pathways in both the short and long term following IR exposure. However studies using various antioxidants to counteract the adverse effects of IR in normal tissues were not fruitful, providing only partial protection. Tocotrienols, especially γ-tocotrienol (GT3) and δ-tocotrienol (DT3), are among the few most promising compounds and have shown striking effects in protecting against radiation damage both as a radioprotectant and as a radiomitigator. A single injection of δ-tocotrienol (DT3) has a dose reduction factor (DRF) of 1.27 as a radioprotectant and 1.1 as a radiomitigator; while γ-tocotrienol (GT3) has a DRF of 1.29 as a radioprotector. In addition, these tocols are non-toxic at effective doses. Studies suggest numerous mechanisms by which GT3 and DT3 exert their radioprotective effects, including the enhancement of eNOS activity via regulation of tetrahydrobiopterin availability and prevention of DNA damage to hematopoietic stem and progenitor cells via stimulation of mTOR survival pathways. Unfortunately both compounds are difficult to purify and thus are in short supply and very expensive. Most tocotrienol rich oils available contain very substantial amounts of tocopherols that may interfere with the bioavailability and bioactivity of the tocotrienols.

Rice bran oil deodorizer distillate (RBODD) is a byproduct from the process of refining rice and is usually discarded. It is rich in tocols, including the active γ- and δ-tocotrienols. It also contains squalene, which has been shown to possess radioprotective capacity. This study examined the tocotrienol rich fraction of rice bran (TRFRB) isolated from rice bran deodorizer distillate, a rice oil refinement waste product, to determine its protective effects against IR induced oxidative damage and $H_2O_2$. Several cell lines were treated with tocotrienols or TRFRB prior to or following exposure to $H_2O_2$ or IR. To determine the radioprotective capacity cells were analyzed for morphology, mitochondrial bioenergetics, clonogenic survival, glutathione oxidation, cell cycle, and migration rate. TRFRB displayed similar antioxidant activity compared to pure tocotrienols. Cells pretreated with TRFRB or DT3 exhibited preserved cell morphology and mitochondrial respiration when exposed to $H_2O_2$. Oxidized glutathione was decreased in TRFRB treated cells exposed to IR. TRFRB reversed mitochondrial uncoupling and protected migration rates following IR exposure. The protective antioxidant capacity of TRFRB treated cells against oxidative injury was similar to that of purified DT3. TRFRB effectively protects normal cells against IR induced injury suggesting that rice bran distillate may be an inexpensive and abundant alternate source.

TRFRB is a standardized extract derived from rice bran oil deodorized distillate that contains GT3 and squalene. Because radiation-induced mitochondrial damage and oxidative stress impacts several critical biologic parameters such as DNA damage repair and stem cell fate, in this research we have compared the effects of treatment with 5 µM GT3 and TRFRB extract against radiation induced mitochondrial dysfunction and oxidative stress. Furthermore, the same treatment preserved the cell viability and mitochondrial respiration in these cells when followed by oxidative insult via $H_2O_2$ treatment. Methods of making TRFRB extract and methods of using these compositions are provided herein.

The rice bran oil deodorized distillate extract called TRFRB extract provided herein is made by an adaptation of the method depicted by Ko et al., Euro J Lipid Science Technol 110:914-919 (2008). Other methods of extracting oil from an oilseed such as a cold or hot press via extruders or presses may also be utilized. TRFRB extract is suitably stored at 4° C. until used and may be concentrated via condensation or dehydration methods know to those of skill in the art. The preparation of the TRFRB composition may include further enrichment and purification using chromatographic techniques using normal or reverse stationary phases and mixtures of solvents such as acetone, ethylene dichloride, hexane, isopropyl alcohol, propyl alcohol, methyl-alcohol, methylene chloride, trichloroethylene, and water. Those of skill in the art will appreciate that the precise chromatography methods can be altered to obtain separated tocotrienol compositions. The TRFRB extract compositions were then analyzed by gas chromatography mass spectroscopy to produce the graphs of FIG. 2. Finally, the extract compositions were standardized by mixing two extracts of known concentrations in the proper proportions to achieve the extract with the target composition. For the standardization one extract has a concentration above target and the other below target. Having, an extract of standard composition is very important from the pharmaceutical point because content uniformity is necessary for accurate dosing.

The TRFRB compositions have total tocotrienol content between 15% and 95%. Suitably at least 30%, 40%, 45%, 50%, 55%, 60%, 70%, 80%, 90% or 95% of the composition is tocotrienols. Suitably, the compositions have less than 30% tocopherols, suitably less than 25%, less that 20%, or even less tocopherols. The tocopherols may decrease the effectiveness of the tocotrienols on the methods of treatment described herein. Pharmaceutical compositions comprising the TRFRB extracts described herein are also provided. The TRFRB also contains substantial amounts of squalene. The squalene content of the compositions may be at least 20% of the composition. Suitably the concentration is at least 25%, 30% or even 35% of the total composition. The compositions provided herein contain a mix of tocotrienols. The tocotrienols are α-tocotrienol and β-γ-tocotrienol. The tocotrienols are found in a ratio of α-tocotrienol to β-γ-tocotrienol of 2:1 to 1:2, suitably 1.5:1 to 1:1.5 or 1.3:1 to 1:1.3 or 1.2:1 to 1:1.2, or 1:1.

The compositions described herein may be used in methods of treating subjects. The compositions may be used to treat subjects in need of a radioprotectant, radiomitigator or for treatment of radiation exposure. In addition, the compositions may be used to treat subjects in need of treatment with an antioxidant agent, an anti-inflammatory agent, an immunoregulatory agent, an anti-thrombotic agent, an anti-atherogenic agent, a hypocholesterolemic agent or an HMG-CoA reductase inhibitor. The methods of treatment are based on administering an effective amount of the compositions provided herein to subjects in need of such treatment. The compositions may be used to treat a subject with a condition selected from the group consisting of radiation exposure, cancer, cardiovascular disease including but not limited to coronary artery disease, elevated lipoprotein levels, elevated cholesterol levels, elevated triglycerides, age-related macular degeneration, cataracts, glaucoma, chronic pain, chronic fatigue syndrome, fever, edema, diabetes mellitus, signs of aging, rheumatoid diseases, septic shock, and Alzheimer's disease.

Methods of protecting cells from oxidative damage or radiation exposure are also provided herein. The methods include contacting the cells with an effective amount to protect the cells from oxidative damage or radiation exposure. The cells can be contacted with the pharmaceutical composition prior to, during, at the same time as, or after oxidative damage or radiation exposure. Cells may be contacted with the agent directly or indirectly in vivo, in vitro, or ex vivo. Contacting encompasses administration to a cell, tissue, mammal, patient, or human. Further, contacting a cell includes adding an agent to a cell culture. Other suitable methods may include introducing or administering an agent to a cell, tissue, mammal, or patient using appropriate procedures and routes of administration as defined below.

The compositions may be used to make pharmaceutical compositions. Pharmaceutical compositions comprising the compositions described above and a pharmaceutically acceptable carrier are provided. A pharmaceutically acceptable carrier is any carrier suitable for in vivo administration. Examples of pharmaceutically acceptable carriers suitable for use in the composition include, but are not limited to, water, buffered solutions, glucose solutions, oil-based or bacterial culture fluids. Additional components of the compositions may suitably include, for example, excipients such as stabilizers, preservatives, diluents, emulsifiers and lubricants. Examples of pharmaceutically acceptable carriers or diluents include stabilizers such as carbohydrates (e.g., sorbitol, mannitol, starch, sucrose, glucose, dextran), proteins such as albumin or casein, protein-containing agents such as bovine serum or skimmed milk and buffers (e.g., phosphate buffer). In the Examples dimethyl sulfoxide was used as a diluent. Especially when such stabilizers are added to the compositions, the composition is suitable for freeze-drying or spray-drying. The composition may also be emulsified.

The compositions described herein may be used to treat a subject with a condition selected from radiation exposure, cancer, cardiovascular disease including but not limited to coronary artery disease, elevated lipoprotein levels, elevated cholesterol levels, elevated triglyceride levels, atherosclerosis, ischemia-reperfusion injury and the like, age-related macular degeneration, cataracts, glaucoma, chronic pain, chronic fatigue syndrome, fever, edema, diabetes mellitus, signs of aging, rheumatoid diseases, septic shock, inflammatory diseases, autoimmune diseases or Alzheimer's disease. In the case of radiation exposure, the compositions may be delivered as a radioprotective agent to a subject prior to potential exposure to radiation, such as to a patient receiving radiation therapy, or a person working with or cleaning up radiation or a radiation spill or leak. The compositions may also be given after radiation exposure as a radiomitigator, such as after an accident involving the release of radiation.

Treatment of a condition includes but is not limited to, prophylaxis of symptoms or indicators of the condition, reduction in disease severity, or reversal, reduction or slowing in disease progression as compared to an untreated subject. The compositions described herein may be used to treat subjects in need of treatment with a radioprotectant, an antioxidant, an anti-inflammatory, immunoregulatory, anti-thrombotic, antiatherogenic, hypocholesterolemic or an HMG-CoA reductase inhibitor. Combination therapy with a known antioxidant, anti-inflammatory or HMG-CoA reductase inhibitor may result in increased effectiveness of the combination treatment as compared to treatment with either composition alone.

The compositions described herein may be administered by any means known to those skilled in the art, including, but not limited to, oral, topical, intranasal, intraperitoneal, parenteral, intravenous, intramuscular, subcutaneous, intrathecal, transcutaneous, nasopharyngeal, intra-lesional, intra-tumoral, intradermal, or transmucosal absorption. Thus the compositions may be formulated as an ingestible, injectable, topical or suppository formulation. The compositions may also be delivered with in a liposomal or time-release vehicle. Administration of the compositions to a subject in accordance with the invention appears to exhibit beneficial effects in a dose-dependent manner. Thus, within broad limits, administration of larger quantities of the compositions is expected to achieve increased beneficial biological effects than administration of a smaller amount. Moreover, efficacy is also contemplated at dosages below the level at which toxicity is seen.

It will be appreciated that the specific dosage administered in any given case will be adjusted in accordance with the compositions being administered, the disease to be treated or inhibited, the condition of the subject, and other relevant medical factors that may modify the activity of the compositions or the response of the subject, as is well known by those skilled in the art. For example, the specific dose for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the composition of the invention and of a known agent such as tocopherol, such as by means of an appropriate conventional pharmacological or prophylactic protocol.

The maximal dosage for a subject is the highest dosage that does not cause undesirable or intolerable side effects. The number of variables in regard to an individual prophylactic or treatment regimen is large, and a considerable range of doses is expected. The route of administration will also impact the dosage requirements. It is anticipated that dosages of the composition will reduce symptoms of the condition at least 10%, 20%, 30%, 40%, 50%, 60%, 70%, 80%, 90% or 100% compared to pre-treatment symptoms or symptoms if left untreated. It is specifically contemplated that pharmaceutical preparations and compositions may palliate or alleviate symptoms of the disease without providing a cure, or, in some embodiments, may be used to cure the disease or disorder.

Suitable effective dosage amounts for administering the compositions may be determined by those of skill in the art, but typically range from about 1 microgram to about 100,000 micrograms per kilogram of body weight weekly, although they are typically about 1,000 micrograms or less per kilogram of body weight weekly. Like other vitamin E compounds, large doses may be required for therapeutic effect and toxicity is likely low. In some embodiments, the effective dosage amount ranges from about 10 to about 10,000 micrograms per kilogram of body weight weekly. In another embodiment, the effective dosage amount ranges from about 50 to about 5,000 micrograms per kilogram of body weight weekly. In another embodiment, the effective dosage amount ranges from about 75 to about 1,000 micrograms per kilogram of body weight weekly. The effective dosage amounts described herein refer to total amounts administered, that is, if more than one composition is administered the effective dosage amounts correspond to the total amount administered. The composition can be administered as a single dose or as divided doses. For example, the composition may be administered two or more times separated by 4 hours, 6 hours, 8 hours, 12 hours, a day, two days, three days, four days, one week, two weeks, or by three or more weeks.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

EXAMPLES

Materials and Methods
Cell Culture

H9c2 rat cardiomyoctes and immortalized human skin keratinocyte cell line (HaCaT) were kindly donated by Dr. Marsh (UAMS) and Dr. Domann (UIOWA) respectively. Primary human dermal fibroblasts were purchased from LifeLine Cell Technologiees (Frederick, Md.) and rat liver microsomes were purchased from BD Biosciences. All cell lines were grown in Dubelco's Minimal Essential Medium containing high glucose and supplemented with 1 mM sodium pyruvate (Gibco), 10% FBS (Hyclone), and 1% L-glutamine (Gibco) in the presence of 1% penicillin and streptomycin. Cells were maintained and experiments were accomplished in a humidified incubator at 37° C. with 5% $CO_2$. For mitochondrial respiration studies, culture media in cells were changed to unbuffered DMEM supplemented with 4 mM Glutamate and incubated in a non-$CO_2$ incubator for 1 h at 37° C., before they were placed in XF96 Extracellular Flux Analyzer. In all experiments, where DMSO used as vehicle, its final concentration in the tissue culture dishes was kept at 0.1% or less (v/v).

Preparation of TRFRB (Tocotrienol-Rich Fraction of Rice Bran)

TRFRB was prepared by rice bran oil deodorizer distillate (RBODD) by an adaptation of the method described by Ko et al., The concentration of tocols from rice bran oil deodorizer distillate using solvent. *European Journal of Lipid Science and Technology* 2008, 110, 914-919. RBODD, provided by Riceland Foods (Stuttgart, Ark.), was refluxed with acetonitrile in a 1:10 ratio. After refluxing, samples were cooled to ambient temperature and stored at −20° C. for 24 hr to precipitate the cold insoluble sterols from the soluble tocols. The sterols were filtered using a sintered glass filter, the filtrate was collected and the solvent evaporated using a Speed Vac concentrator. Samples were then mixed with an ethanolic solution containing 5% (w/v) pyrogallol and the mixture was refluxed to boiling. Tocols were saponified at 70° C. for 30 min following the addition of 1 mL of 50% (w/v) aqueous potassium hydroxide solution. After cooling in an ice water bath the mixture was transferred to a 500-ml separatory funnel, and 30 ml diethyl ether and 20 ml distilled water were added. The diethyl ether extraction was repeated two times and the ether fractions were pooled. The pooled diethyl ether was washed three times with 20 ml distilled water, and then filtered through anhydrous sodium sulfate for 30 min to remove any excess water. The diethyl ether was evaporated using the Speed Vac concentrator to obtain the tocotrienol rich fraction of rice bran (TRFRB).

Qualitative and Quantitative Analysis of TRFRB

Composition of TRFRB was determined by a gas chromatography/mass spectrometry (GC/MS) method. For this analysis, samples of the extract were analytically transferred to deactivated glass micro-inserts using methylene chloride, dried under nitrogen, and derivatized using N-methyl-N-TMS-trifluoroacetamide (Restek CO., Bellefonte Pa.) at 25° C. Analyses were performed by GC/MS using Agilent 5975 GC/MSD (Agilent Technologies, Santa Clara, Calif.). The GC was equipped with a 30-m HP-5MS column (0.250 mM, 0.25 µM). Samples were analyzed using helium as the carrier gas (head pressure of 27 psi), 1 µl splitless injection, the injector temperature was 275° C., the column temperature was maintained at 220° C. for 2 min followed by a gradient of 25° C./min to 300° C., remaining at that temperature for 10 min. The transfer line temperature was maintained at 285° C. for 13.5 min followed by a gradient of 25° C./min to 300° C., remaining at that temperature for 10 min. The MS conditions were: electron impact, source temperature 230° C., quadrupole temperature 150° C., and ionization voltage 70 eV. The identity of the tocols in the rice extract was established by comparing the retention time and mass spectra of authentic samples of each tocol (Yasoo Health, Jonesborough, Tenn.). Quantitation of the derivatized tocols was performed in triplicate using single-ion monitoring. The MS ions detected were 416 (δ-tocotrienol), 410 (α-tocopherol) and 424 (β-γ-tocotrienol); 223, 256, 376 were the confirming ions respectively. All the bioassays were conducted using proper dilutions of stock solution of TRFRB in DMSO standardized to 20 mM content of tocotrienols (9.8 mM GT3/BT3 and 8.6 mM of AT3)

TBARS Assay:

The antioxidant activity of TRFRB was assessed measuring the ability to prevent microsomal lipid peroxidation. For this a TBARS assay was performed using a modified version of the original method described by Buege and Aust, Microsomal lipid peroxidation. *Methods Enzymol* 1978, 52, 302-310. Briefly, rat liver microsomes (BD Bioscience) were suspended in PBS in glass tubes at final concentration of 1 mg/mL. To this, increasing concentrations of TRFRB dissolved in DMSO were added. DMSO alone was used as control. The final DMSO percentage was kept under 0.1%. Microsomes were subsequently incubated with the test compounds at 37° C. for one hour in a shaking water bath (100 rpm). After one hour, freshly made tert-Butyl hydroperoxide (TBHP) solution was added to microsomes at a final concentration of 200 µM and incubation was continued for another 30 mins. The reaction was terminated by addition of 20% trichloroacetic acid and tubes were placed on ice for 15 mins. Equal volume of 0.67% thiobarbituric acid in 0.05N NaOH was added and the final mixture was heated at 95° C. for 45 mins to allow the color to develop. Finally, the tubes were cooled on ice and centrifuged at 1000 rpm for 20 mins and the supernatant was read at 532 nm. The percent TBARS was calculated using a standard curve obtained using malondialdehyde (MDA). The results in the figure are expressed in µM of tocotrienols and compared with the effects of pure gamma-tocotrienol.

Cell Morphology

H9c2 rat heart cardiomyocytes were treated with either vehicle control (DMSO, 0.1% v/v), 5 µM delta-tocotrienol or 5 µM TRFRB overnight. Cells were then exposed to 100 or 200 µM $H_2O_2$ for 4 h. Morphological changes were recorded under an inverted microscope. Pictures were taken at 10× magnification. Scale bar represents 400 µm.

Mitochondrial Bioenergetics

Oxygen consumption rate (OCR) was measured at 37° C. using an XF96 extracellular analyzer (Seahorse Bioscience) as previously described Pathak et al., *Antioxid Redox Signal* 2014, 20, 1436-1446. H9c2 rat heart cardiomyocytes cells were plated in 96 well Seahorse plates. The next day they were treated with either vehicle (DMSO, 0.1% v/v) or 5 µM of DT3 or 5 µM of TRFRB overnight. The cells were then treated with 50 or 100 µM $H_2O_2$ for 4 h at 37° C. The media in the wells were changed to unbuffered DMEM supplemented with 4 mM Glutamate and incubated in a non-$CO_2$ incubator for 1 h at 37° C. Three baseline measurements were acquired before injection of mitochondrial inhibitors or unbouplers. Readings were taken after sequential addition of oligomycin (10 µM), carbonylcyanide 4-(trifluoromethoxy) phenylhydrazone (FCCP, 10 µM) and rotenone/antimycin A (10 µM). Oxygen consumption rates were calculated by the Seahorse XF-96 software and represent an average of 3 measurements on 8 different wells. The rate of measured oxygen consumption was reported as pmol $O_2$ consumed per minute per 10,000 cells.

In order to determine the radioprotective effects of TRFRB, human immortalized keratinocytes (HaCaT cells) were plated in 96 well Seahorse plates. The next day they were treated with either vehicle (DMSO, 0.1% v/v) or 5 µM of DT3 or 5 µM of TRFRB overnight. The Seahorse plates were either sham irradiated or irradiated with 8 Gy of γ-irradiation. Both plates were sequentially run in the XF96 extracellular analyzer as described above.

In vitro Scratch Assay

Human immortalized keratinocytes (HaCaT cells) were plated in 12 well culture plates and irradiated with 8 Gy or sham irradiated 24 h after plating. The cells were given either vehicle (DMSO, 0.1% v/v) or 5 µM of DT3 or 5 µM of TRFRB 4 hours following radiation. Culture media were replaced again at 36 h following radiation. At the 72 h time point, a scratch was made using a sterile micropipette tip in each well. This created an open area into which the keratinocytes migrated. Two areas of the scratch margins were imaged daily until scratches were closed. The area of the scratch remaining was measured on the images at five points per field, with two fixed fields averaged using Cell Analyzer 1.0 (BWTech, Iowa City, Iowa). Measurements were stopped when cells no longer made positive progress towards the scratch origin. See Ross et al., *Exp Dermatol* 2011, 20, 58-63.

Clonogenic Cell Survival

Human immortalized keratinocytes (HaCaT cells) were plated and irradiated with 8 Gy or sham irradiated 24 h after plating. The cells were given either vehicle (DMSO, 0.1% v/v) or 5 µM of DT3 or 5 µM of TRFRB 4 h following radiation. Culture media were replaced again at 36 h following radiation. At the 72 h time point, the cells were trypsinized and plated at various dilutions for clonogenic survival. Cells were fixed in 70% ethanol and stained with Coomassie blue 14 d later. Clones with more than 50 cells were counted under dissecting microscope. See Aykin-Burns et al., *Biochem J* 2009, 418, 29-37.

Measurements of Glutathione and Glutathione Disulfide Levels

Human dermal fibroblasts were plated in 100 mm plates and next day they were treated with (DMSO, 0.1% v/v) or 5 µM of DT3 or 5 µM of TRFRB for 16 h. The cells were then irradiated 8 Gy. Cell pellets were collected 24 hours following irradiation and pipette-homogenized in 50 mM $PO_4$ buffer pH 7.8 containing 1.34 mM diethylenetriaminepentaacetic acid [DETAPAC buffer]. Total glutathione content was determined as previously described using the Anderson method Greenwald *Crc handbook of methods for oxygen radical research*. CRC Press: Boca Raton, Fla., 1985; p 447. To distinguish reduced glutathione [GSH] and glutathione disulfide [GSSG], 2 µl of a 1:1 mixture of 2-vinylpyridine and ethanol was added per 30 µl of sample and assayed as described previously Griffith *Anal Biochem* 1980, 106, 207-212. All glutathione determinations were normalized to the protein content of whole homogenates using the Lowry et al. method *J Biol Chem* 1951, 193, 265-275.

Statistical Analysis:

Statistical analysis was performed using GraphPad Prism 5.0 (GraphPad Software, San Diego, Calif.). Data were expressed as mean±SD unless otherwise specified. One-way ANOVA analysis with Tukey's post analysis was used to study the differences among 3 or more means. Significance was determined at p<0.05 and the 95% confidence interval.

RESULTS

Figure 1:
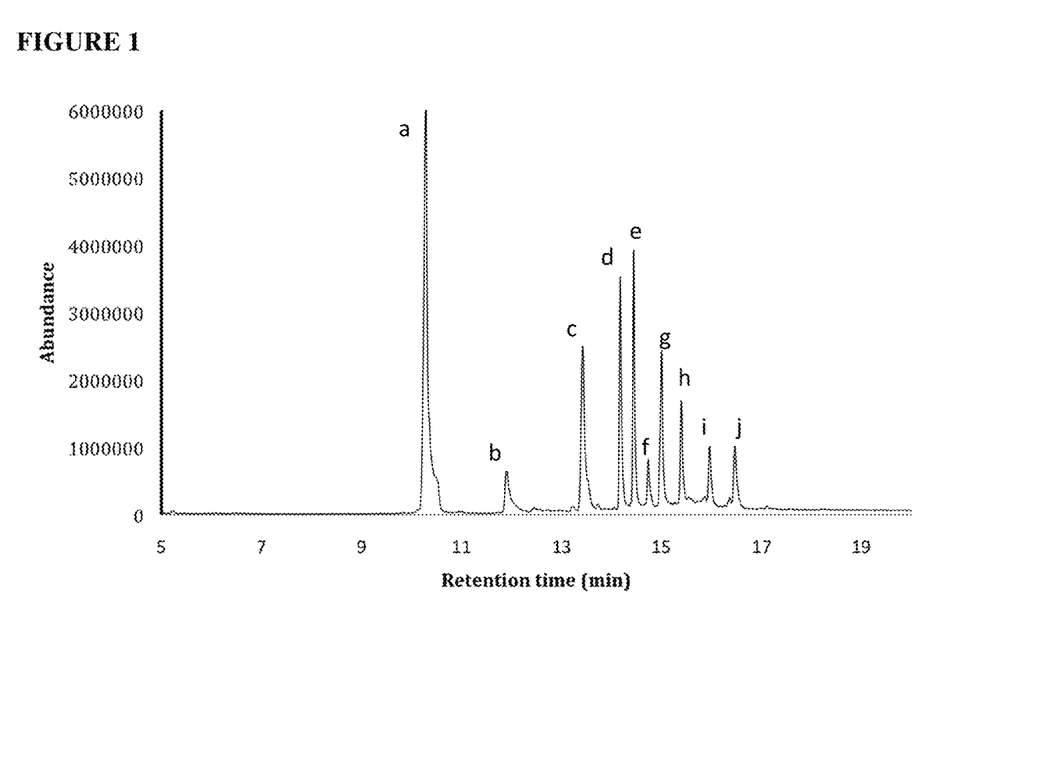
FIG. 1 shows the gas chromatography/mass spectroscopy (GC/MS) profiles of the tocol rich fraction derived from rice bran oil deodorized distillate. The peaks labels are as follows: (a) squalene. (b) δ-tocopherol, (c) β- and γ-tocopherol, (d) α-tocopherol, (e) β- and γ-tocotrienol, (f) campesterol, (g) α-tocotrienol, (h) β-sitosterol, (i) cycloartenol, and (j) 2,4-methylenecycloartenol.

A full SCAN GC/MS analysis demonstrated approximately 17.3% of tocotrienols, 25.3% of tocopherols, and 31.2% of squalene (FIG. 1, Table 1).

TABLE 1

Chemical composition of TRFRB determined via GC/MS

| COMPOUND | Tocopherol | Tocotrienol | Other |
|---|---|---|---|
| δ-tocopherol | 4.3 | | |
| β-γ tocopherol | 11.7 | | |
| α-tocopherol | 9.3 | | |
| β-γ tocotrienol | | 9.2 | |
| α-tocotrienol | | 8.1 | |
| Squalene | | | 31.2 |
| Campestrol | | | 3.2 |
| Sitosterol | | | 5.2 |
| Cycloartenol | | | 3.7 |
| 2,4-methylenecycloartenol | | | 4 |
| TOTAL % | 25.3 | 17.3 | 47.3 |

Figure 2:
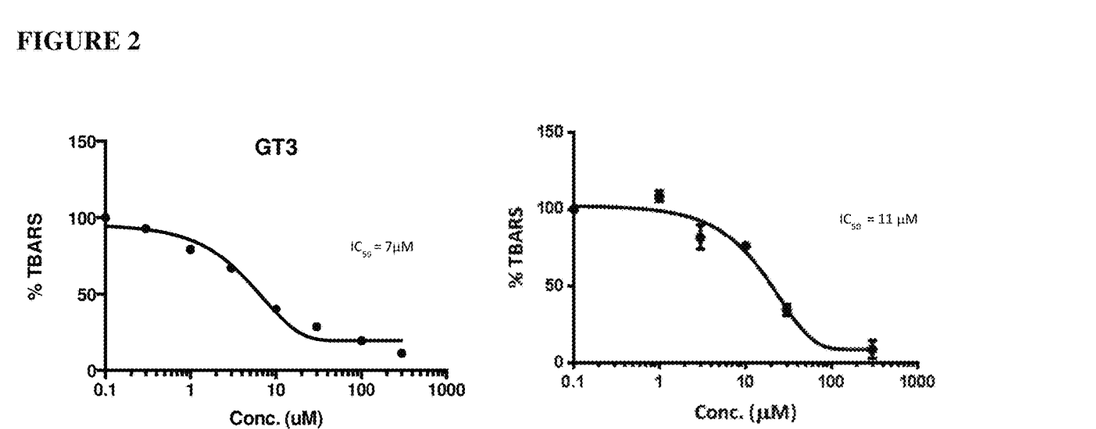
FIG. 2 shows a graph of the ability of GT3 (gamma-tocotrienol) and TRFRB (tocol-rich fraction of rice bran) to inhibit TBHP induced lipid peroxidation in Wistar rat liver microsomes as a measure of the antioxidant activity by TBARS analysis.

In order to determine the $IC_{50}$ of TRFRB and GT3, the rat liver microsomes were pretreated with 0.5, 1, 5, 10, 50, 100, and 500 µM of pure GT3 or TRFRB for 1 h. The microsomes were then subjected to a powerful oxidant TBHP for an additional 30 min. $IC_{50}$ values for both are calculated as the concentration that reduced the amount of lipid peroxidation approximately 50%. The $IC_{50}$ values were 7 µM and 11 µM for pure GT3 and TRFRB respectively; suggesting a comparable antioxidant capacity of TRFRB similar to pure GT3 against TBHB induced lipid peroxidation (FIG. 2).

Figure 3:
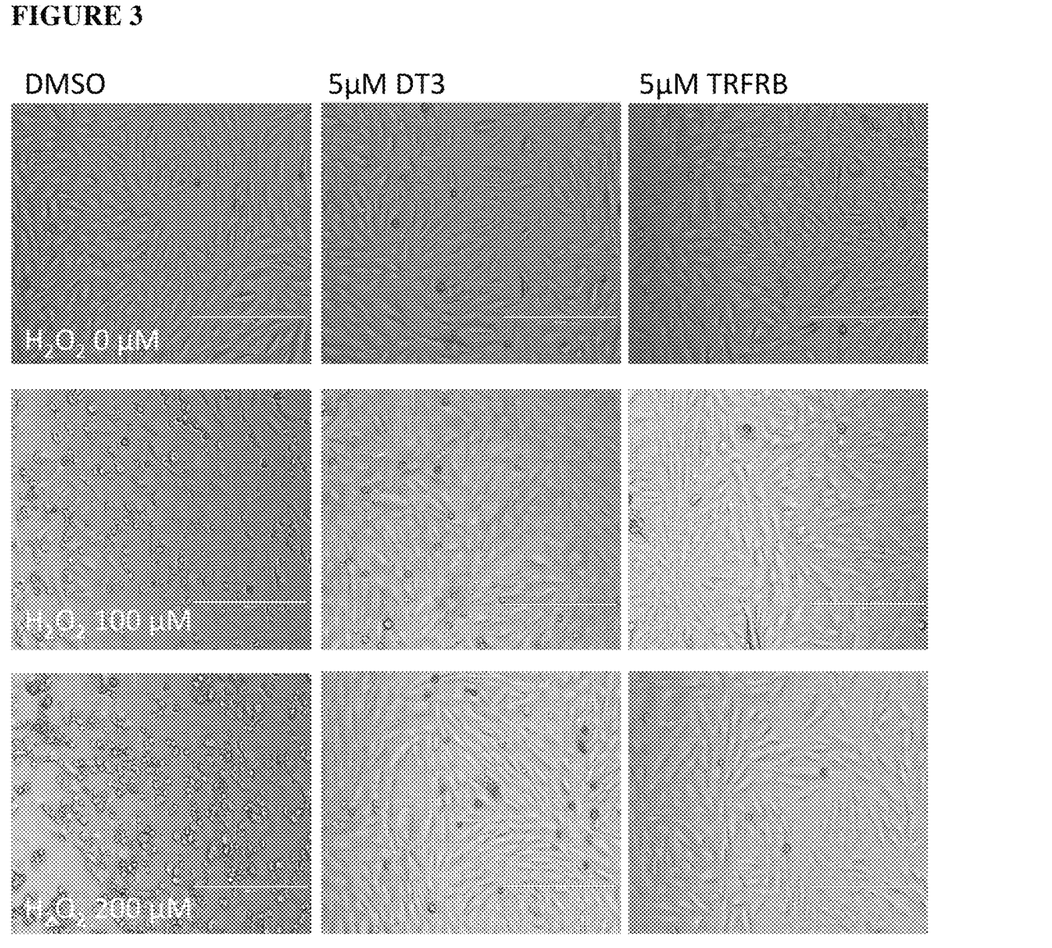
FIG. 3 is a set of photographs showing the protection of cardiomyocytes from hydrogen peroxide damage after the indicated treatments. Pre-treatment with 5 μM DT3 or TRFRB significantly protected the cell morphology against $H_2O_2$ treatment. Pictures were taken at 10× magnification. The scale bar represents 400 μm.

We then investigated whether TRFRB can protect the various cells types from different tissue origins against $H_2O_2$ or IR induced oxidative damage. Pretreatment of H9c2 rat heart cardiomyocytes with 5 µM of DT3 or TRFRB significantly protected the morphology of these cells from 4 h of 100 and 200 µM $H_2O_2$ treatment (FIG. 3), suggesting that TRFRB is as effective as a pure tocotrienol isomer against peroxide induced cell injury.

Figures 4, 4A:
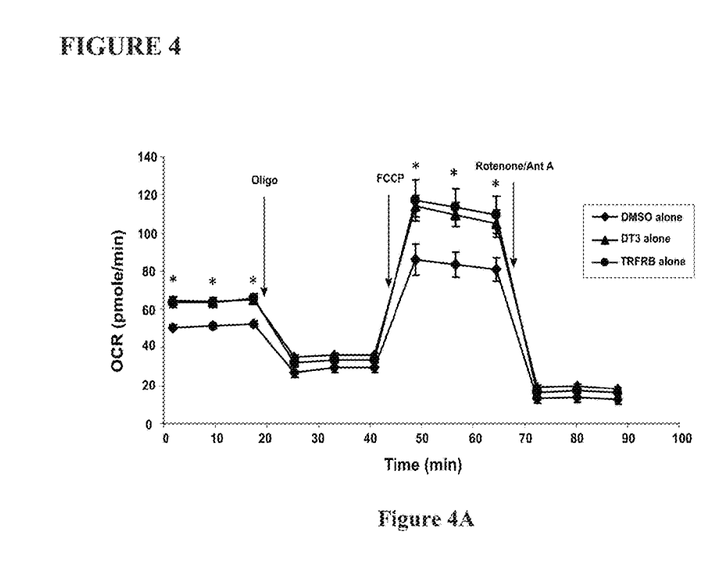
Figure 4B:
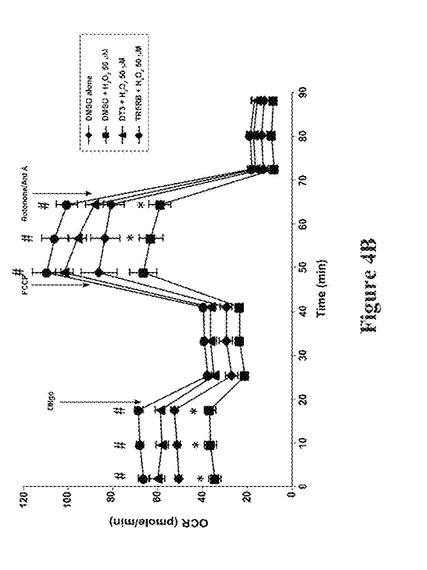
Figure 4C:
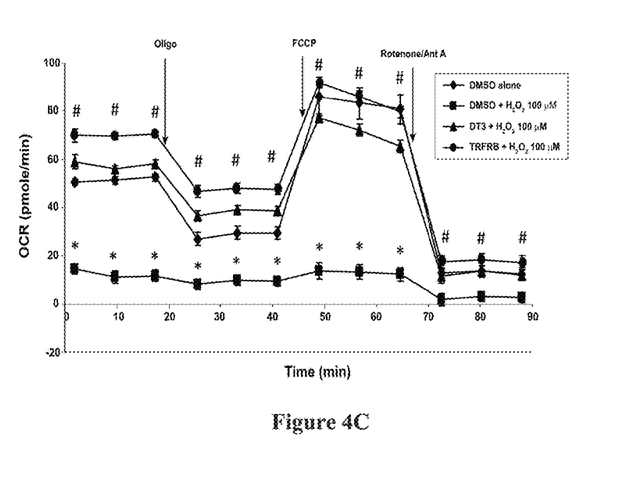

We and others have previously shown that IR induced oxidative stress significantly and adversely effects mitochondrial electron transport chain and respiration. Therefore, the next experiment assessed the effects of TRFRB and pure DT3 on cellular bioenergetics and mitochondrial respiration in the absence of any cellular stress. Intracellular mitochondrial function was examined by sequentially adding inhibitors of oxidative phosphorylation. Initially we took 3 measurements to determine the "basal respiration" of the cells. By injecting an inhibitor of mitochondrial ATP synthase (oligomycin), a decrease in oxygen consumption rate (OCR) was obtained and this decrease in OCR is termed as "ATP linked respiration". In order to determine the maximal respiration potential of the cells, FCCP, an uncoupler, was used. Immediately following FCCP injection, oxygen consumption increased and cells reached to their maximum respiration. Mitochondrial "reserve respiratory capacity" was calculated by subtracting the maximum OCR from the basal OCR. Overnight (16 h) treatment of both DT3 and TRFRB increased basal oxygen consumption rate (OCR) as well as maximum OCR in H9c2 rat heart cardiomyocytes (FIG. 4A). When H9c2 cells treated with additional 4 h of 50 µM $H_2O_2$, the basal, the ATP linked and maximum OCR were significantly decreased compared to the control group. 100 µM $H_2O_2$ treatment for 4 h completely halted the cellular respiration (FIGS. 4B and C). Treatment with 5 µM of DT3 or TRFRB for 16 h prior to 50 or 100 µM $H_2O_2$ resulted in complete protection and restored the mitochondrial respiration of these cells (FIGS. 4B and C).

Figure 5:
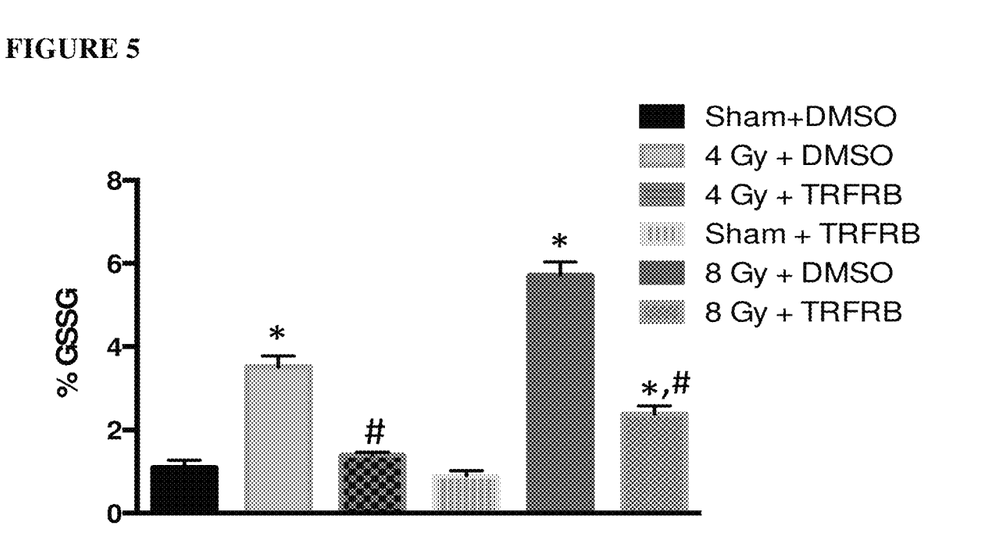
FIG. 5 shows that oxidized glutathione levels in dermal fibroblasts were increased at 72 h when the cells were exposed to 4 or 8 Gy IR. This increase was prevented when cells received 5 μM TRFRB 24 h before IR. Each data point represents mean±SD of n=3 treatment dishes. *$p<0.001$ as compared to Sham DMSO group #$p<0.001$ as compared to IR treated group.

Next we extended our findings into a different cell type and different cellular injury. Since therapeutic irradiation can result in significant skin injury, we focused on two different skin cell types to determine whether TRFRB can protect human skin cells from IR induced stress. First primary human dermal fibroblast (HDF) cells were irradiated at different doses and 24 h following IR the cells were collected to measure glutathione (GSH) and glutathione disulfide (GSSG) levels. Additional 2 sets of samples were also collected to be analyzed for cell cycle or re-plated for clonogenic cell survival assay. Both 4 and 8 Gy IR significantly increased the percentage of GSSG over total GSH suggesting an increase in oxidative stress in HDFs at these two IR doses. Pretreatment with 5 µM TRFRB reversed this effect and significantly decreased the % GSSG levels in HDFs (FIG. 5).

Figure 6:
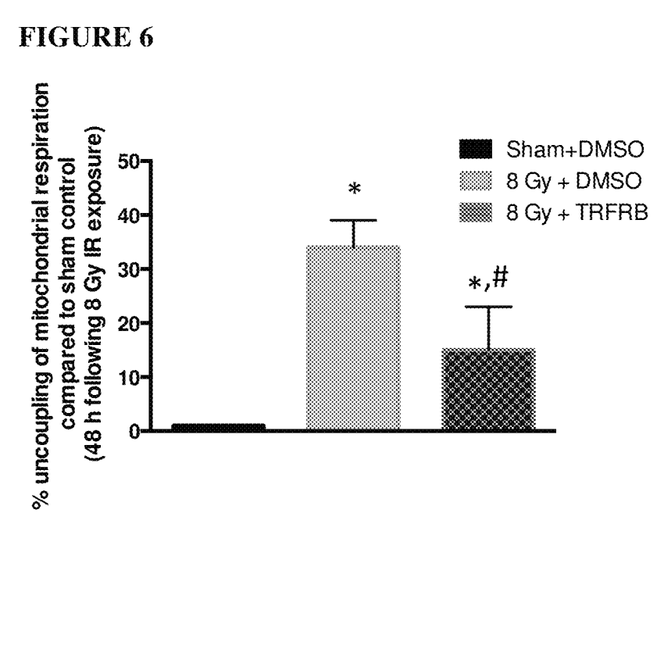
FIG. 6 is a graph showing that the degree of mitochondrial uncoupling of HaCaT cells was significantly increased at 48 h when exposed to 8 Gy IR and this increase was reversed in the presence of 5 μM DT3 or TRFRB. Each data point represents mean±SEM of n=8-16 wells from 2 separate experiments. *$p<0.001$ as compared to Sham DMSO group. **$p<0.05$ as compared to Sham DMSO group, #$p<0.05$ as compared to IR treated group.

Secondly we utilized an immortalized human skin keratinocyte line (HaCaT cells) to evaluate the radioprotective effects of TRFRB. HaCaT cells were pretreated with DMSO vehicle or 5 µM of DT3 or TRFRB for 16 h prior to 8 Gy IR. Then the cellular bioenergetics and mitochondrial respiration in these cells were assayed at 48 h following IR exposure as described with H9c2 cells. The percent mitochondrial uncoupling is defined and calculated by determining the increase in the ratio of basal respiration to maximum respiration (OCR following FCCP treatment) and the data was normalized to the sham irradiated control group. The degree of mitochondrial uncoupling of HaCaT cells was significantly increased at 48 h when exposed to 8 Gy IR and this increase was partially but significantly reversed in the presence of 5 µM TRFRB pretreatment (FIG. 6).

Figure 7:
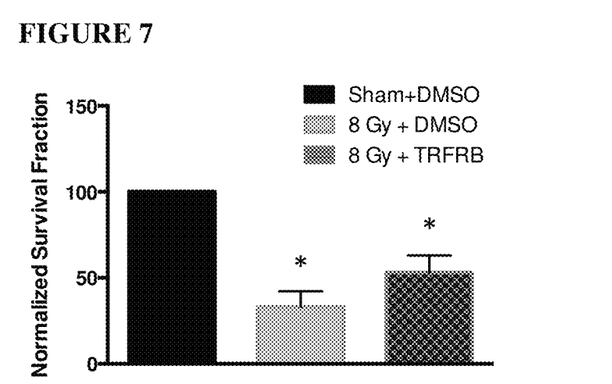
FIG. 7 is a graph showing that when HaCaT cells were irradiated with 8 Gy IR, received DT3 or TRFRB 4 h post irradiation, and plated for clonogenic cell survival 72 h following IR, there was an increase in cell survival in TRFRB treated cells. However, this increased survival fraction was not statistically significant compared to 8 Gy IR alone group. Each data point represents mean±SD of n=3 treatment dishes. *p<0.001 as compared to Sham DMSO group.
Figure 8:
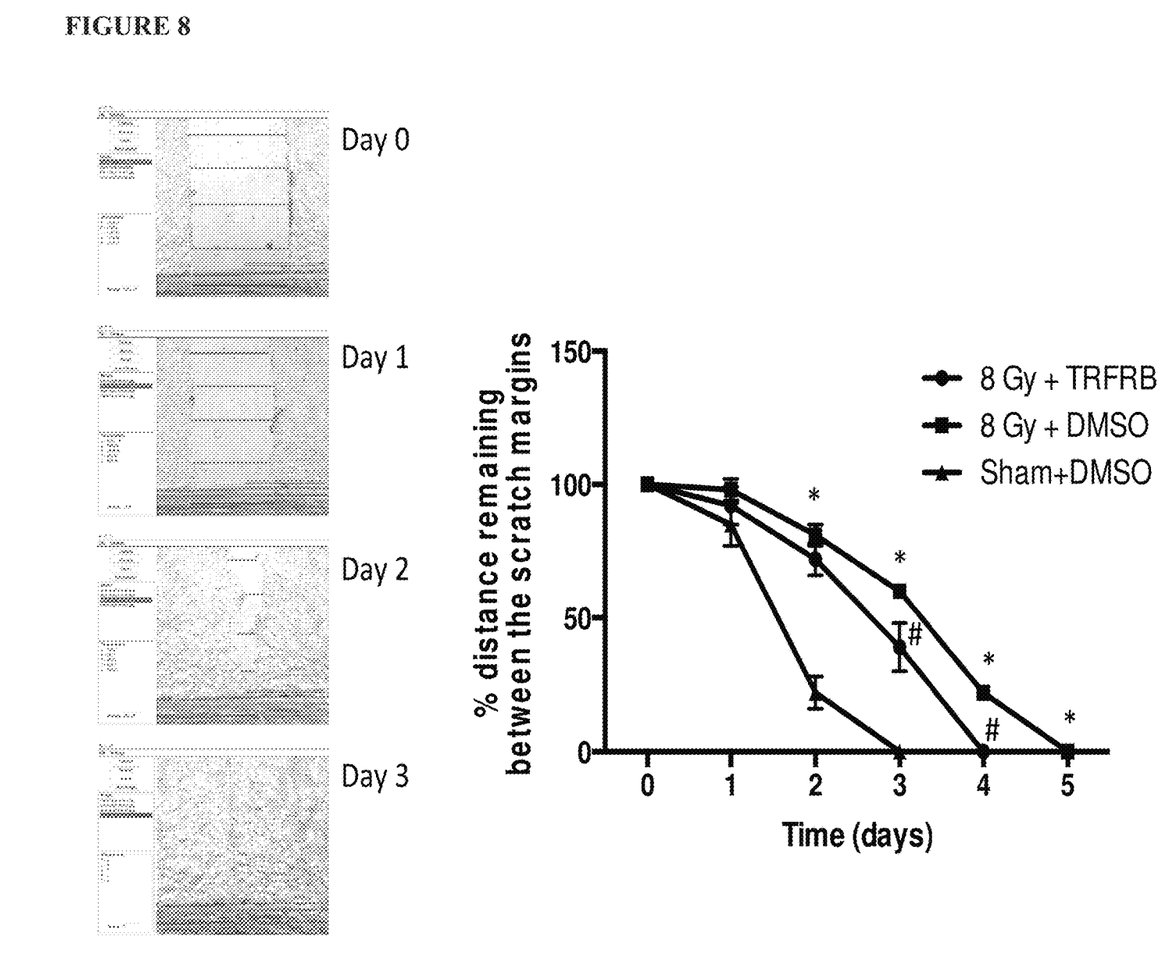
FIG. 8 shows a set of photographs and a graph showing the results of a scratch assay. Migration rates of HaCaT cells were decreased when the cells were exposed to 8 Gy IR. This decrease was partially restored when cells received 5 µM DT3 or TRFRB 4 h after IR exposure. Each data point represents mean±SD of five points per field, with two fixed fields (n=10)

In our next set of experiments we wanted to determine whether TRFRB could protect the skin cells from IR induced injury even if TRFRB is given after IR exposure. When HaCaT cells were irradiated with 8 Gy IR, received DT3 or TRFRB 4 h post irradiation, and plated for clonogenic cell survival 72 h following IR, there was a slight increase in cell survival in TRFRB treated cells. This protection in the increased survival fraction was not statistically significant compared to 8 Gy IR alone group (FIG. 7). An in vitro scratch assay was utilized to evaluate the protective efficacy of TRFRB for keratinocyte migration function when the cells were treated with TRFRB after IR exposure. Migration rates of HaCaT cells were significantly improved (although they did not completely reach the levels of DMSO vehicle group) even if the cells were treated 4 h after 8 Gy IR exposure (FIG. 8).

There is a significant and unmet need for the development of alternative strategies and novel agents to alleviate radiation side effects. The only approved radioprotective agent amifostine has limited use due to its side effects. Tocotrienols, Vitamin E analogs, have been gaining a great deal of attention in the past decade as radioprotectors for radiotherapy patients as well as in the context of accidental exposures of large populations. Their unsaturated isoprenoid side chain differentiates tocotrienols from tocopherols, which are less efficacious in protection against ionizing radiation. In addition to their antioxidant properties, the tocotrienols have been shown to increase tetrahydrobiopterin levels thus increase eNOS activity. They also effectively inhibit 3-hydroxy-3-methylglutaryl-coenzyme A (HMG-CoA) reductase enzyme, enhance hematopoietic recovery, reduce intestinal radiation injury, and accelerate the recovery of soluble markers of endothelial function. Despite their superb radioprotective effects however tocotrienols (DT3 and GT3) are in short supply and very expensive to purify. It is in this context that a byproduct of rice oil refinement could provide a viable alternative source for isolation of tocotrienols in large quantities.

Here we provide evidence that a tocotrienol-rich fraction of rice bran oil deodorizer distillate, TRFRB, shows efficacy against peroxide and ionizing radiation induced injury in vitro. TRFRB demonstrated a significant antioxidant function against hydroperoxide induced lipid peroxidation in rat liver microsomes, which was comparable to that of pure GT3.

Various cultured cell models were also utilized to explore which attributes of TRFRB were required for protection against $H_2O_2$ and IR induced cell damage in cardiomyoctes, epidermal keratinocytes as well as dermal fibroblasts. TRFRB demonstrated a profound effect preserving the morphology of cardiomycoytes against $H_2O_2$ exposure. TRFRB also protected the human dermal fibroblasts cells from IR induced oxidative stress by preventing the oxidation of glutathione following IR exposure. Interestingly, epidermal keratinocytes treated with TRFRB post irradiation, demonstrated a slight increase in clonogenic cell survival. More importantly migration rates of keratinocytes were significantly improved by TRFRB treatment even though they received TRFRB 4 h after exposure to IR. Additional TRFRB treatment of these cells at 36 h following radiation exposure probably fortified and protected the keratinocytes from IR-induced late ROS effects. This is significant since keratinocyte migration is a crucial component of wound healing, which is known to be perturbed when skin is exposed to IR.

Our mitochondrial function and cellular respiration studies also revealed significant effects of TRFRB on cells with or without any cellular stress. Oxygen consumption rates of the cells were measured using the XF96 extracellular flux analyzer. The increases measured in basal and maximal OCR suggests that both DT3 and TRFRB enhanced cellular respiration, which could be due to an increase in mitochondrial biogenesis or enhanced function of existing mitochondria. Our calculations also demonstrated an increase in reserve respiratory capacity of the cells implying that TRFRB and DT3 improve the ability to respond against any stress that might increase the energy demand in the cell. This supposition was validated when the cells were exposed to two powerful stressors, $H_2O_2$ or IR. In both cases, pretreatment of cardiomyocytes or skin keratinocytes with TRFRB exhibited significant protection of mitochondrial function.

Collectively these results strongly suggest that the antioxidant capacity of TRFRB was critical to its ability to protect cells from oxidative injuries (via $H_2O_2$ or IR). Our cellular bioenergetics studies also suggest that TRFRB protects the cells against IR injury by partly preserving the cells' mitochondrial function.

We claim:

1. A method of treating a subject in need of a radioprotectant, a radiomitigator, or a treatment for radiation exposure comprising administering an effective amount of a pharmaceutical composition to the subject, the pharmaceutical composition comprising an extract of rice bran oil deodorizer distillate and a pharmaceutically acceptable carrier,
   wherein the extract of rice bran oil deodorizer distillate comprises at least 15% tocotrienols and at least 15% tocopherols,
   wherein the extract of rice bran oil deodorizer distillate comprises α-tocopherol, β-tocotrienol, and γ-tocotrienol in a weight ratio of (i) α-tocopherol to (ii) β-tocotrienol and γ-tocotrienol between 1:2 and 2:1, and
   wherein the extract of rice bran oil deodorizer distillate has a squalene concentration at least 15% by weight.

2. The method of claim 1, wherein the pharmaceutical composition is administered prior to radiation exposure.

3. The method of claim 1, wherein the pharmaceutical composition is administered after radiation exposure.

4. The method of claim 1, wherein the extract of rice bran oil deodorizer distillate further comprises β-tocopherol, γ-tocopherol, δ-tocopherol, α-tocotrienol, squalene, or any combination thereof.

5. The method of claim 1, wherein the extract has a total tocotrienol concentration between 15% and 80% by weight.

6. The method of claim 1, wherein the pharmaceutically acceptable carrier is an oil-based fluid.

7. A method of treating a subject in need of a radioprotectant, a radiomitigator, or treatment for radiation exposure comprising administering an effective amount of a pharmaceutical composition, the pharmaceutical composition comprising an extract of rice bran oil deodorizer distillate and a pharmaceutically acceptable carrier,
   wherein the extract of rice bran oil deodorizer distillate has a tocopherol component comprising α-tocopherol and a tocotrienol component comprising (i) α-tocotrienol and (ii) β-tocotrienol and γ-tocotrienol in a weight ratio of (i) α-tocopherol to (ii) β-tocotrienol and γ-tocotrienol between 1:2 and 2:1, and
   wherein the weight ratio of the tocopherol component to tocotrienol component is at least 1:2, and
   wherein the extract of rice bran oil deodorizer distillate has a squalene concentration at least 15% by weight.

8. The method of claim 7, wherein the weight ratio of tocopherol component to α-tocotrienol, β-tocotrienol, or γ-tocotrienol is at least 1:1.

9. The method of claim 7, wherein the weight ratio of α-tocopherol to α-tocotrienol, β-tocotrienol, or γ-tocotrienol is at least 1:1.

10. The method of claim 7, wherein the tocopherol component further comprises β-tocopherol, γ-tocopherol, δ-tocopherol, or any combination thereof.

11. The method of claim 7, wherein the pharmaceutical composition is administered prior to radiation exposure.

12. The method of claim 7, wherein the pharmaceutical composition is administered after radiation exposure.

13. A method of treating a subject in need of a radioprotectant, a radiomitigator, or a treatment for radiation exposure comprising administering an effective amount of a pharmaceutical composition, the pharmaceutical composition comprising an extract of rice bran oil deodorizer distillate and a pharmaceutically acceptable carrier;
wherein the extract of rice bran oil deodorizer distillate comprises α-tocopherol, β-tocopherol and/or γ-tocopherol, δ-tocopherol, α-tocotrienol, β-tocotrienol and/or γ-tocotrienol, and squalene;
wherein the extract of rice bran oil deodorizer distillate has a weight ratio of (i) α-tocopherol to (ii) β-tocotrienol and/or γ-tocotrienol between 1:2 and 2:1, and
wherein the extract of rice bran oil deodorizer distillate has a squalene concentration at least 15% by weight.

14. The method of claim 13, wherein the pharmaceutical composition is administered prior to radiation exposure.

15. The method of claim 13, wherein the pharmaceutical composition is administered after radiation exposure.

16. The method of claim 13, wherein the weight ratio of (i) α-tocopherol, β-tocopherol, γtocopherol, and δ-tocopherol to (ii) β-tocotrienol, γ-tocotrienol, α-tocotrienol is greater than 1:1.

17. The method of claim 16, wherein the extract of rice bran oil deodorizer distillate comprises at least 15% tocotrienols and at least 15% tocopherols.

18. The method of claim 13, wherein the pharmaceutically acceptable carrier is an oil-based fluid.

* * * * *